US010407415B2

(12) United States Patent
Yamashita et al.

(10) Patent No.: US 10,407,415 B2
(45) Date of Patent: *Sep. 10, 2019

(54) DIHYDRATE OF BENZOTHIOPHENE COMPOUND OR OF A SALT THEREOF, AND PROCESS FOR PRODUCING THE SAME

(71) Applicant: OTSUKA PHARMACEUTICAL CO., LTD., Chiyoda-ku, Tokyo (JP)

(72) Inventors: Hiroshi Yamashita, Osaka (JP); Tetsuya Sato, Osaka (JP); Takuya Minowa, Osaka (JP); Yusuke Hoshika, Osaka (JP); Hidekazu Toyofuku, Osaka (JP); Tetsuya Yamaguchi, Osaka (JP); Masahiro Sota, Osaka (JP); Shuuji Kawano, Osaka (JP); Takayuki Nakamura, Osaka (JP); Ryohei Eto, Osaka (JP); Takuma Ikebuchi, Osaka (JP); Kei Moriyama, Osaka (JP); Nobuaki Ito, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/294,644

(22) Filed: Oct. 14, 2016

(65) Prior Publication Data

US 2017/0066752 A1 Mar. 9, 2017

Related U.S. Application Data

(63) Continuation of application No. 14/396,224, filed as application No. PCT/JP2013/062681 on Apr. 23, 2013, now Pat. No. 9,499,525.

(60) Provisional application No. 61/636,920, filed on Apr. 23, 2012, provisional application No. 61/791,378, filed on Mar. 15, 2013.

(51) Int. Cl.
*C07D 409/12* (2006.01)
*A61K 9/00* (2006.01)

(52) U.S. Cl.
CPC .......... *C07D 409/12* (2013.01); *A61K 9/0019* (2013.01)

(58) Field of Classification Search
CPC .................................................. C07D 409/12
See application file for complete search history.

(56) References Cited

U.S. PATENT DOCUMENTS

| 7,888,362 | B2 | 2/2011 | Yamashita et al. | |
| 9,499,525 | B2* | 11/2016 | Yamashita | C07D 409/12 |
| 2008/0280914 | A1 | 11/2008 | Serno et al. | |
| 2010/0178344 | A1 | 7/2010 | Lambert et al. | |
| 2010/0285476 | A1 | 11/2010 | Rusche et al. | |
| 2011/0003002 | A1 | 1/2011 | Petersen et al. | |
| 2011/0152286 | A1 | 6/2011 | Yamashita et al. | |

FOREIGN PATENT DOCUMENTS

| EP | 2 868 318 A1 | 5/2015 |
| JP | 2006-316052 | 11/2006 |
| WO | WO 2005/041937 A2 | 5/2005 |
| WO | WO 2006/030446 A1 | 3/2006 |
| WO | WO 2012/026562 A1 | 3/2012 |

OTHER PUBLICATIONS

English-language International Search Report from European Patent Office in corresponding International Application No. PCT/JP2013/062681 dated Jul. 18, 2013.
English-language written opinion of the International Search Authority from the European Patent Office In corresponding International Application No. PCT/JP2013/062681 dated Jul. 18, 2013.
Pullar et al., "LY367265, An Inhibitor of the 5-Hydroxytryptamine Transporter and 5-Hydroxytryptamine.sub.2A Receptor Antagonist: A Comparison With the Antidepressant, Nefazodone", European Journal of Pharmacology, vol. 407, pp. 39-46 (2000).
Svensson, ".alpha,-Adrenoceptor Modulation Hypothesis of Antipsychotic Atyicality", Progress in Neuro-Psychopharmacology & Biological Psychiatry, vol. 27, pp. 1145-1158 (2003).
Toru et al., "Creativity in the Development of the Drug, Aripiprazole: A Novel Partial Dopamine D.sub.2 Receptor Agonist for the Treatment of Schizophrenia", Seishin-Igaku, (Psychiatry), vol. 46, pp. 855-864, (2004).
Yagcioglu, Turkish Journal of Psychiatry, vol. 18(4), p. 1-10 (2007).
Examination Report for corresponding Indian Patent Application No. 8867/DELNP/2014 dated Jun. 14, 2018.
"Brexpiprazole", old version of the Wikipedia page, edited on Mar. 11, 2012.
T. Kikuchi et al., Society of Biological Psychiatry 2011 Annual Meeting, Biol. Psychiatry 2011; 69: 1 S-290S, Abstract 320, "Preclinical Pharmacology of OPC-34712: A Novel Compound with Dopamine 02 Receptor Partial Agonist Activity".
"Otsuka HD Places Top Priority on Development of OPC-34712", Pharma Japan 2219/Jan. 3, 2011, p. 3.
D. F. Wong et al, Society of Biological Psychiatry 2011 Annual Meeting, Biol. Psychiatry 2011; 69: 1 S-290S, Abstract 619, "A Phase I, Open-Label PET Study of the Pharmacokinetics, Tolerability and D2/D3 Striatal Occupancy of Single-Dose Oral OPC-34712 in Healthy Subjects".
S. Byrn et al.: "Pharmaceutical Solids: A strategic Approach to Regulatory Considerations", Pharmaceutical Research vol. 12, No. 7, 1995, pp. 945-954.
M. E. Aulton, "Pharmaceutics—The Science of Dosage Form Design", Churchill Livingstone, Second Edition 2002, Chapter 9, pp. 141-145.

(Continued)

*Primary Examiner* — Emily A Bernhardt
(74) *Attorney, Agent, or Firm* — Finnegan, Henderson, Farabow, Garrett & Dunner, LLP

(57) ABSTRACT

An object of the present invention is to provide a compound that can be used as a more superior therapeutic agent for central nervous system diseases. The present invention provides a dihydrate of 7-[4-(4-benzo[b]thiophen-4-yl-piperazin-1-yl)butoxy]-1H-quinolin-2-one or of a salt thereof, and a process for producing the same.

3 Claims, 7 Drawing Sheets

(56) References Cited

OTHER PUBLICATIONS

D. E. Braun et al., "Stability of Solvates and Packing Systematics of Nine Crystal Forms of Antipsychotic Drug Aripiprazole". Crystal Growth & Design, 2009, vol. 9, No. 2, pp. 1054-1065.
Notice of opposition dated Aug. 8, 2018, to the European Patent No. 2841431.
Response to Opposition dated Dec. 19, 2018, for the corresponding EP Patent No. 2841431.

* cited by examiner

[Fig. 1]
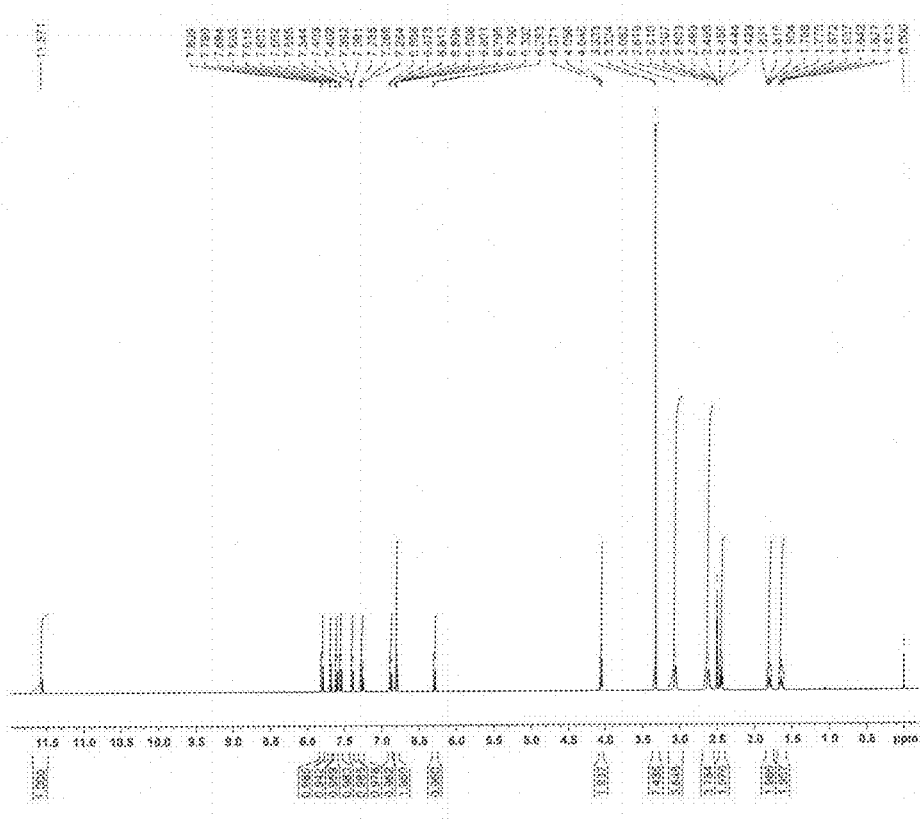
[Fig. 2]
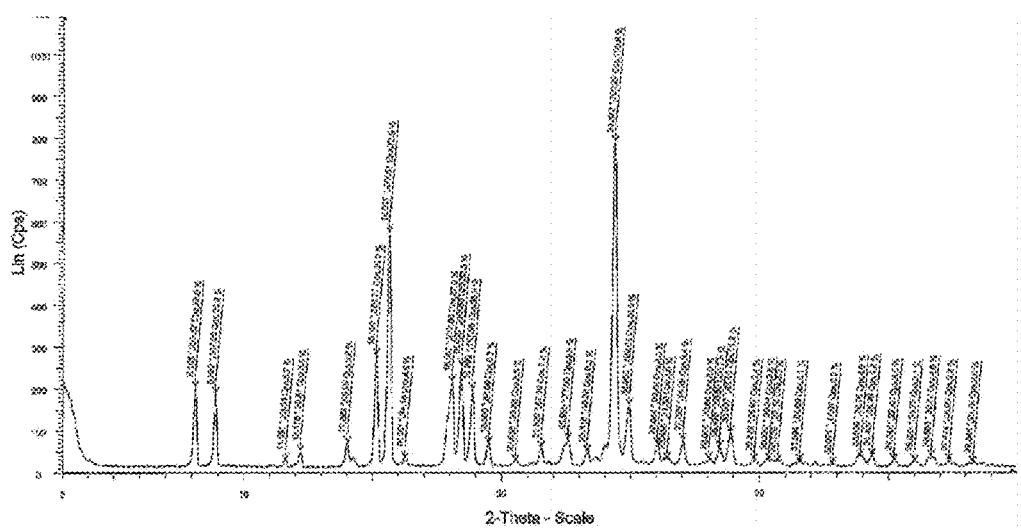

[Fig. 3]
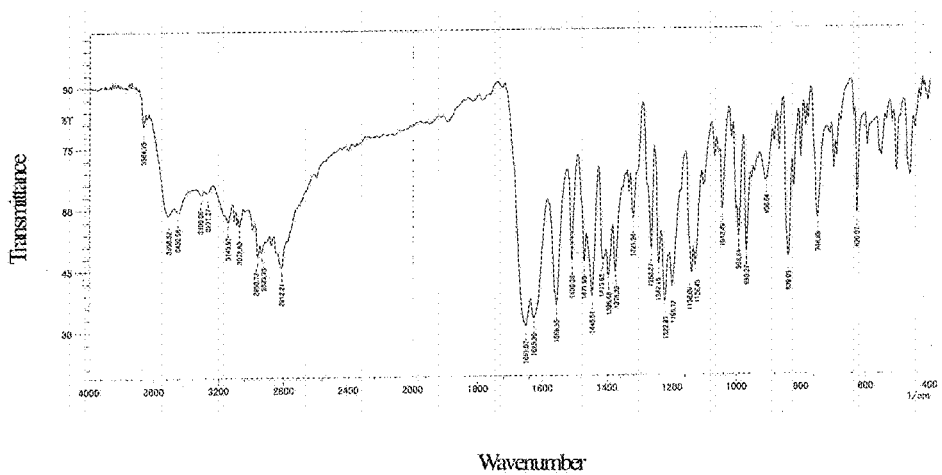
[Fig. 4]
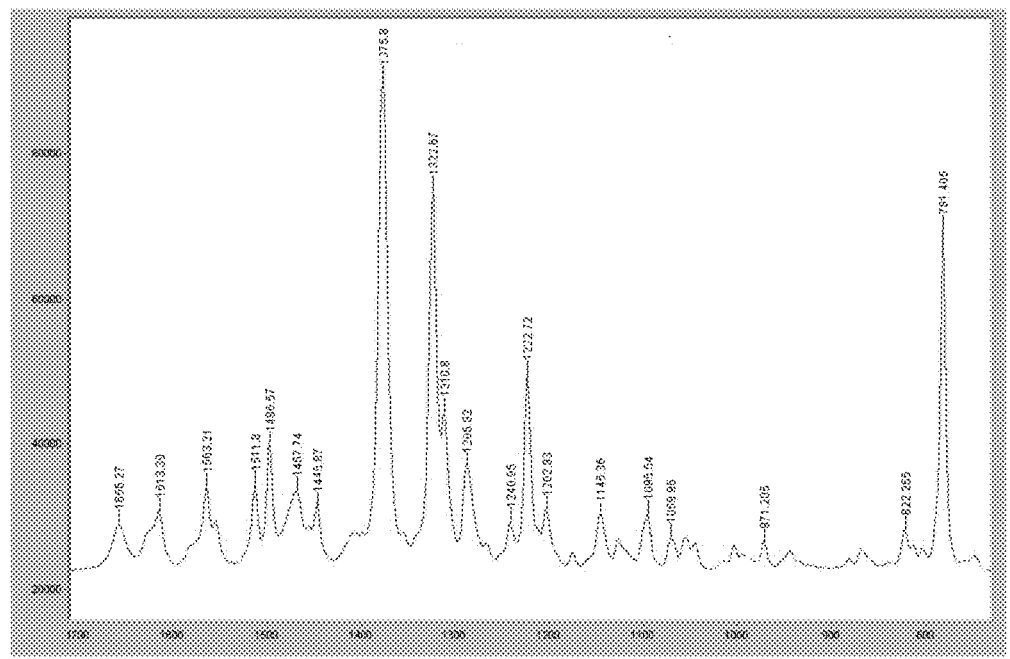

[Fig. 5]
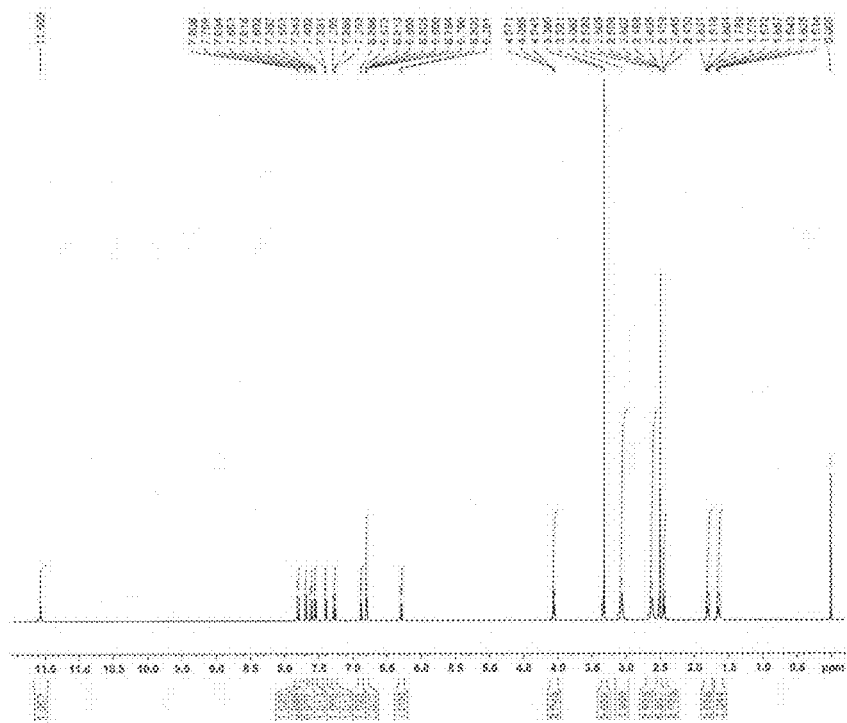
[Fig. 6]
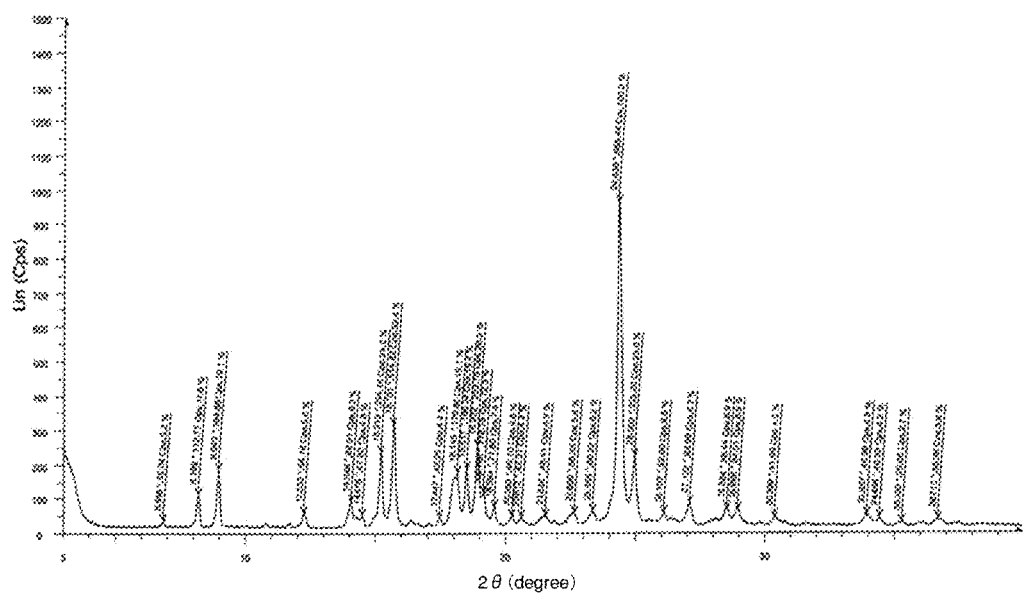

[Fig. 7]
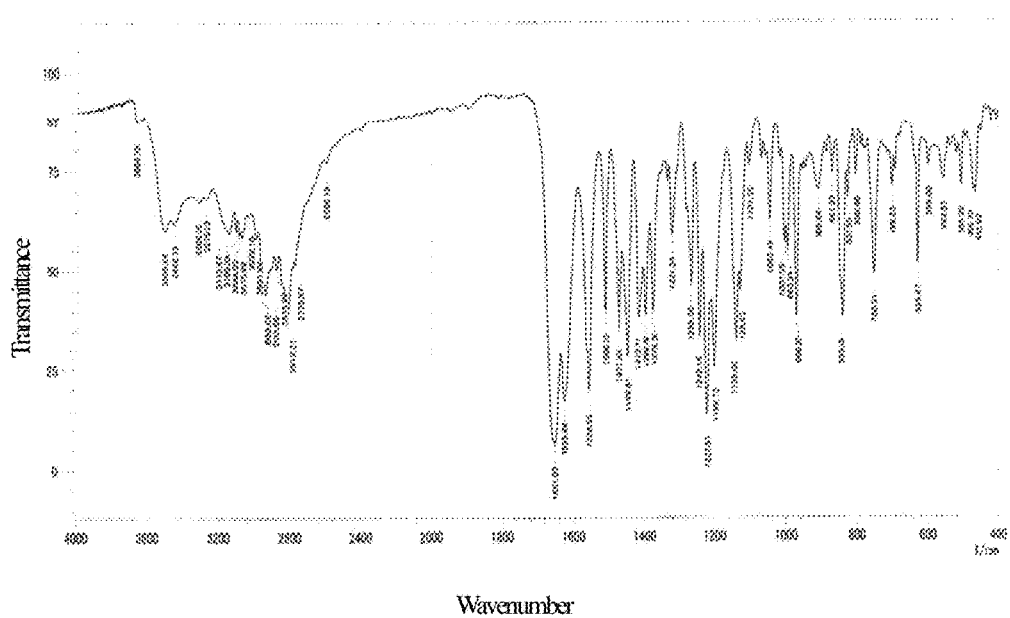
[Fig. 8]
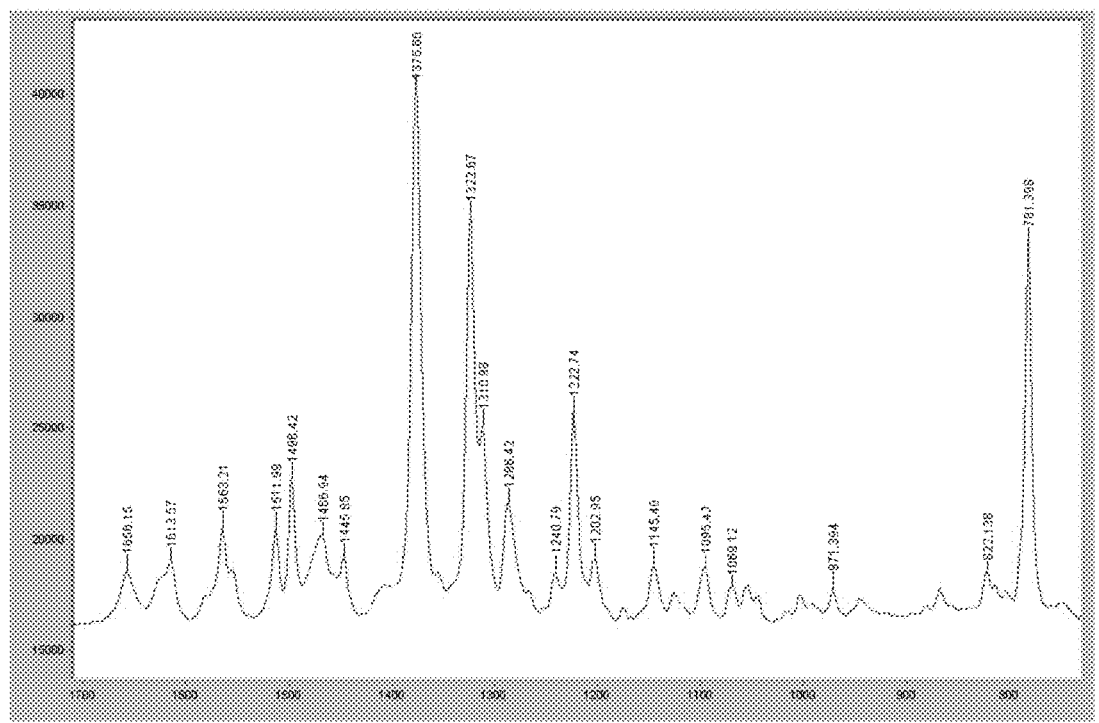

[Fig. 9]
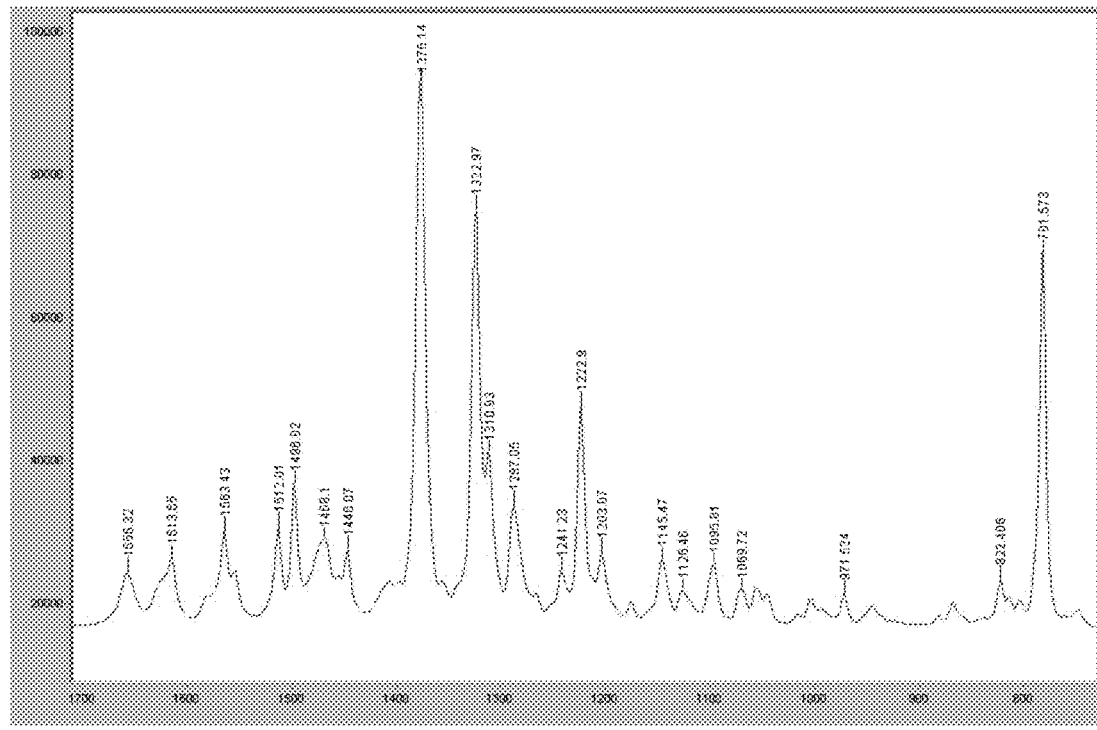
[Fig. 10]
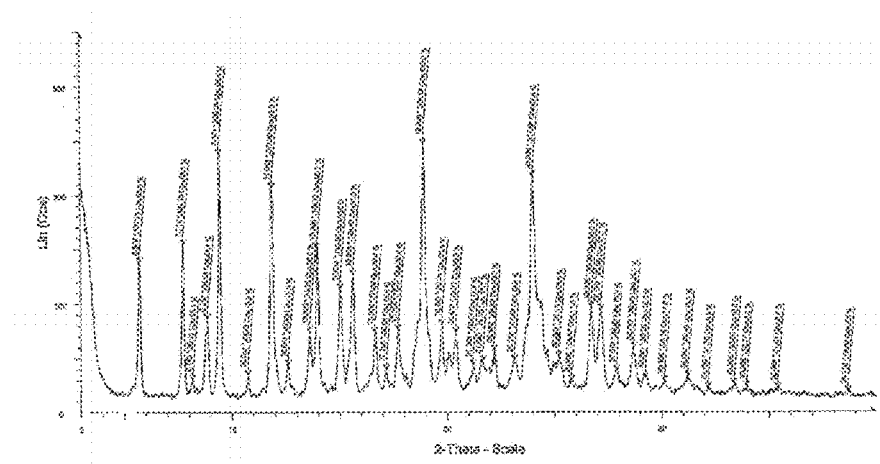

[Fig. 11]
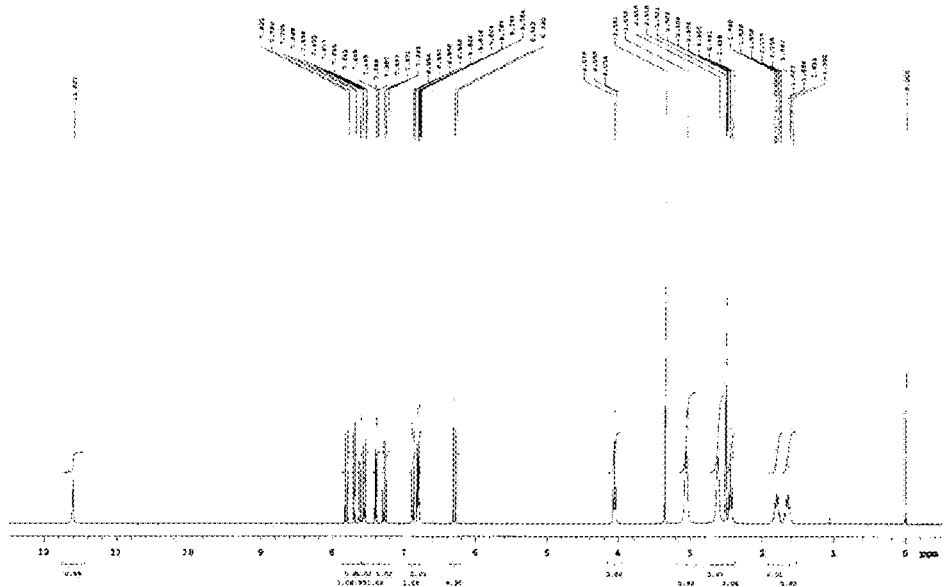
[Fig. 12]
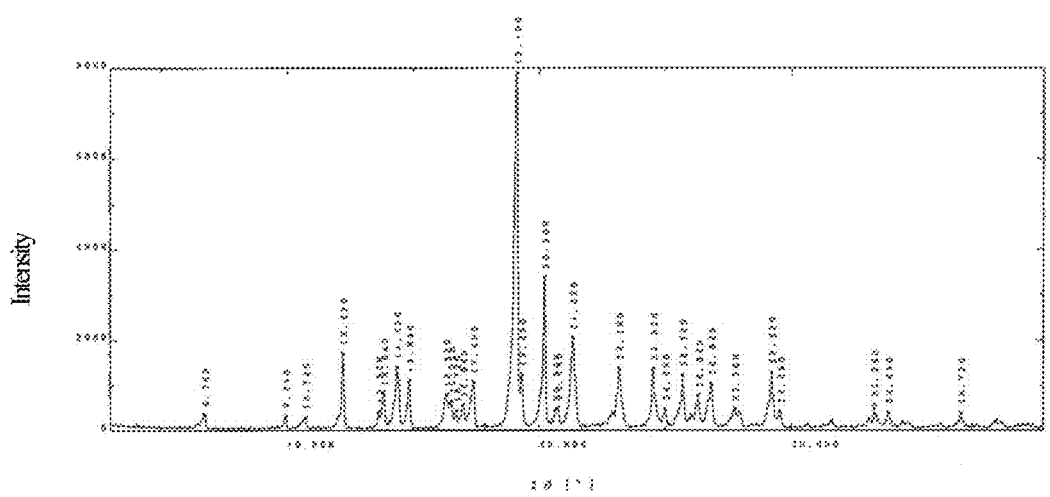

[Fig. 13]
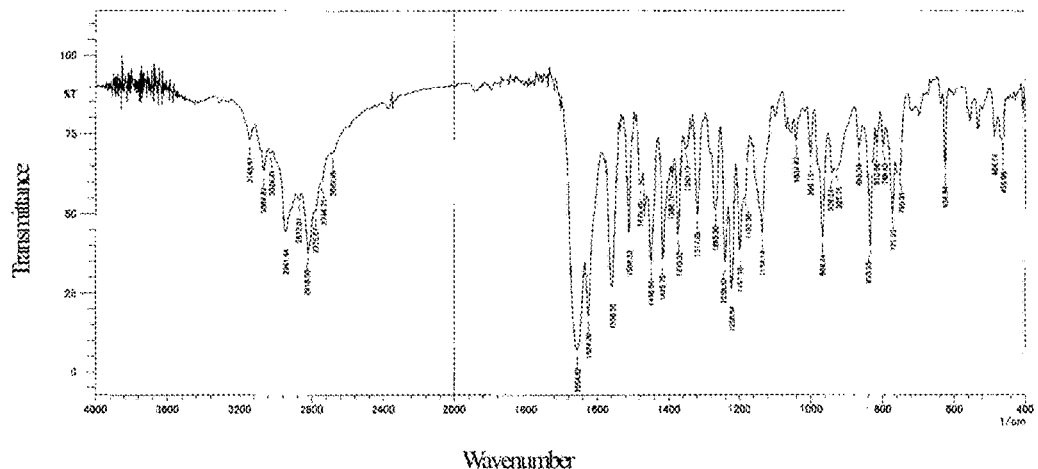
[Fig. 14]
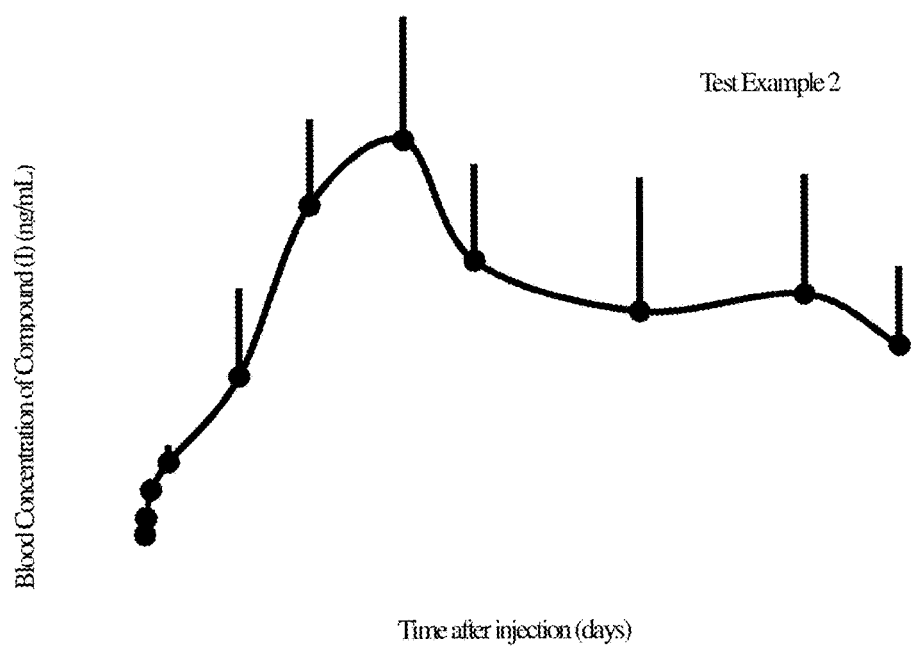

DIHYDRATE OF BENZOTHIOPHENE COMPOUND OR OF A SALT THEREOF, AND PROCESS FOR PRODUCING THE SAME

This is a continuation of Application No. 14/396,224, filed Oct. 22, 2014, which is the National Stage Application of PCT/JP2013/062681, filed Apr. 23, 2013, and claims the benefit of U.S. Provisional Application No. 61/636,920, filed Apr. 23, 2012and U.S. Provisional Application No, 61/791, 378, filed Mar. 15, 2013, all of which are incorporated herein by reference.

TECHNICAL FIELD

The present invention relates to a dihydrate of a benzothiophene compound or of a salt thereof, and a process for producing the same.

BACKGROUND ART

A heterocyclic compound having a specific substituent or substituents is known as an active ingredient that has serotonin uptake inhibitory activity (or serotonin re-uptake inhibitory activity) in addition to dopamine $D_2$ receptor partial agonistic activity ($D_2$ receptor partial agonistic activity), serotonin 5-$HT_{2A}$ receptor antagonistic activity (5-$HT_{2A}$ receptor antagonistic activity), and adrenaline $\alpha_1$ receptor antagonistic activity ($\alpha_1$ receptor antagonistic activity) (Patent Literature (PTL) 1). This active ingredient has a wide therapeutic spectrum for central nervous system diseases (particularly schizophrenia).

In the pharmaceutical field, the development of pharmaceutical preparations that are suitable according to the severity of disease in various patients in need of treatment, patient predisposition, and other factors, has been desired. Although the heterocyclic compound disclosed in the above PTL 1 is known to have a wide therapeutic spectrum for neurological diseases, the development of a more effective therapeutic agent is currently desired.

CITATION LIST

Patent Literature

PTL 1: JP2006-316052A

SUMMARY OF INVENTION

Technical Problem

An object of the present invention is to provide a compound that can be used as a more superior therapeutic agent for central nervous system diseases.

Solution to Problem

The present inventors conducted extensive research to develop a more superior therapeutic agent for central nervous system diseases. As a result, the inventors found that among the heterocyclic compounds disclosed in PTL 1, a specific benzothiophene compound that is in the form of a dihydrate of the benzothiophene compound or of a salt thereof (hereinafter also referred to as the "dihydrate of the present invention") can be the desired therapeutic agent. Further, the present inventors found that when the dihydrate of the present invention is used as an intramuscular injection for treating central nervous system diseases, it functions as a highly effective pharmacologically active substance.

The present invention has been accomplished based on this finding. The present invention provides a novel dihydrate of the benzothiophene compound represented by Formula (I) or of a salt thereof, which is in the form of a hydrate, and further provides an industrially advantageous process for producing the dihydrate.

The present invention provides a novel dihydrate, a process for production thereof, and a benzothiophene compound comprising the dihydrate shown in items 1 to 14.

Item 1. A dihydrate of 7-[4-(4-benzo[b]thiophen-4-yl-piperazin-1-yl)butoxy]-1H-quinolin-2-one or of a salt thereof.

Item 2. The dihydrate according to item 1 which has characteristic peaks at diffraction angles (2θ) of 8.1°, 8.9°, 15.1°, 15.6°, and 24.4° in an X-ray powder diffraction pattern measured by copper radiation of λ=1.5418 Å through a monochromator.

Item 3. The dihydrate according to item 1 or 2 which has characteristic peaks at 3509 $cm^{-1}$, 2934 $cm^{-1}$, 2812 $cm^{-1}$, 1651 $cm^{-1}$, 1626 $cm^{-1}$, 1447 $cm^{-1}$, 1223 $cm^{-1}$, and 839 $cm^{-1}$ in an infrared absorption spectrum as measured by a potassium bromide tablet method.

Item 4. The dihydrate according to any one of items 1 to 3 which has characteristic peaks at 1497 $cm^{-1}$, 1376 $cm^{-1}$, 1323 $cm^{-1}$, 1311 $cm^{-1}$, 1287 $cm^{-1}$, 1223 $cm^{-1}$, and 781 $cm^{-1}$ in a Raman spectrum.

Item 5. The dihydrate according to any one of items 1 to 4 which contains water in an amount of 6.5 to 8.8 wt. %.

Item 6. The dihydrate according to any one of items 1 to 5 which has peaks in a $^1$H-NMR spectrum at:
1.64 ppm (tt, J=7.4 Hz, J=7.4 Hz, 2H),
1.80 ppm (tt, J=7.0 Hz, J=7.0 Hz, 2H),
2.44 ppm (t, J=7.5 Hz, 2H),
2.62 ppm (br, 4H),
3.06 ppm (br, 4H),
3.32 ppm (s, 4H+$H_2O$),
4.06 ppm (t, J=6.5 Hz, 2H),
6.29 ppm (d, J=9.5 Hz, 1H),
6.80 ppm (d, J=2.5 Hz, 1H),
6.80 ppm (dd, J=2.5 Hz, J=9.0 Hz, 1H),
6.88 ppm (d, J=7.5 Hz, 1H),
7.27 ppm (dd, J=7.8 Hz, J=7.8 Hz, 1H),
7.40 ppm (dd, J=0.5 Hz, J=5.5 Hz, 1H),
7.55 ppm (d, J=9.0 Hz, 1H),
7.61 ppm (d, J=8.0 Hz, 1H),
7.69 ppm (d, J=5.5 Hz, 1H),
7.80 ppm (d, J=9.5 Hz, 1H), and
11.57 ppm (s, 1H).

Item 7. A process for producing a dihydrate of 7-[4-(4-benzo[b]thiophen-4-yl-piperazin-1-yl)butoxy]-1H-quinolin-2-one or of a salt thereof,
the process comprising:
(1) mixing at least one organic acid selected from the group consisting of acetic acid and lactic acid, an ethanol-water mixed solution, and 7-[4-(4-benzo[b]thiophen-4-yl-piperazin-1-yl)butoxy]-1H-quinolin-2-one to prepare an acid solution;
(2) cooling the solution obtained in step (1) to 5° C. or less; and
(3) mixing the solution cooled in step (2) with an alkali to adjust the pH of the solution to 7 or more.

Item 8. A dihydrate of 7-[4-(4-benzo[b]thiophen-4-yl-piperazin-1-yl)butoxy]-1H-quinolin-2-one or of a salt thereof obtained by the process according to item 7.

Item 9. A benzothiophene compound for use in treating and/or preventing a central nervous system disease, the compound comprising the dihydrate according to any one of items 1 to 6 and 8 and an anhydride of 7-[4-(4-benzo[b]thiophen-4-yl-piperazin-1-yl)butoxy]-1H-quinolin-2-one or of a salt thereof, and the dihydrate being contained in an amount of 60 wt. % or more in the compound.

Item 10. A method for preventing and/or treating a central nervous system disease comprising the dihydrate according to any one of items 1 to 6 and 8 as an active ingredient.

Item 11. The method according to item 10 which is for preventing or treating a central nervous system disease selected from the group consisting of schizophrenia, treatment-resistant, refractory and chronic schizophrenia, emotional disturbance, psychotic disorder, mood disorder, bipolar disorder, mania, depression, endogenous depression, major depression, melancholic and treatment-resistant depression, dysthymic disorder, cyclothymic disorder, anxiety disorder, somatoform disorder, factitious disorder, dissociative disorder, sexual disorder, eating disorder, sleep disorder, adjustment disorder, substance-related disorder, anhedonia, delirium, cognitive impairment, cognitive impairment associated with Alzheimer's disease, Parkinson's disease, and other neurodegenerative diseases, BPSD caused by cognitive impairment, cognitive impairment in schizophrenia, cognitive impairment caused by treatment-resistant, refractory or chronic schizophrenia, vomiting, motion sickness, obesity, migraine, pain, mental retardation, autism, Tourette's syndrome, tic disorder, attention deficit hyperactivity disorder, conduct disorder, and Down's syndrome.

Item 12. A dopamine $D_2$ receptor partial agonist and/or a $5\text{-}HT_{2A}$ receptor antagonist and/or a serotonin uptake inhibitor and/or a serotonin reuptake inhibitor and/or a $\alpha_1$ receptor antagonist comprising the dihydrate according to any one of items 1 to 6 and 8 as an active ingredient.

Item 13. A pharmaceutical composition comprising the dihydrate according to any one of items 1 to 6 and 8 and a pharmaceutically acceptable carrier.

According to another embodiment of the present invention, a hydrate of the benzothiophene compound described below is provided.

Item 14. A hydrate of 7-[4-(4-benzo[b]thiophen-4-yl-piperazin-1-yl)butoxy]-1H-quinolin-2-one which has characteristic peaks at diffraction angles (2θ) of 7.7°, 9.4°, 11.8°, 18.9°, and 24.0° in an X-ray powder diffraction pattern measured by copper radiation of λ=1.5418 Å through a monochromator.

The dihydrate of the present invention and the process for producing the dihydrate are described in detail below.

Process for Producing the Dihydrate of the Benzothiophene Compound or of a Salt Thereof According to the Present Invention The benzothiophene compound referred to in the dihydrate of the benzothiophene compound or of a salt thereof according to the present invention is 7-[4-(4-benzo[b]thiophen-4-yl-piperazin-1-yl)butoxy]-1H-quinolin-2-one represented by Formula (I).

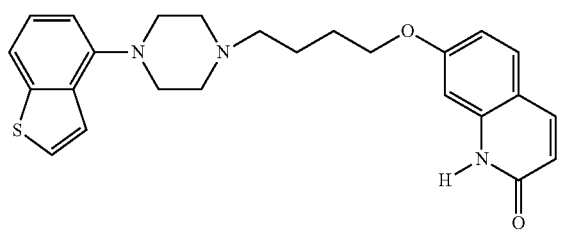

(I)

The dihydrate of the benzothiophene compound represented by Formula (I) or of a salt thereof according to the present invention can be produced from an anhydride of the benzothiophene compound or of a salt thereof.

The benzothiophene compound (in the form of an anhydride) of Formula (I), from which the dihydrate of the present invention is produced, is a known compound, and can be obtained by the production method disclosed in Example 1 of JP2006-316052A or according to Reference Examples 1 and 2 described below herein.

The dihydrate of the benzothiophene compound of Formula (I) or of a salt thereof according to the present invention can be produced by steps (1) to (3) described above.

In step (1), at least one organic acid selected from the group consisting of acetic acid and lactic acid, an ethanol-water mixed solution, and the benzothiophene compound of Formula (I) (in the form of an anhydride) is mixed to prepare an acid solution.

Lactic acid that is used as an organic acid may be D-form, L-form, or a mixture thereof.

The ethanol-water mixed solution used in step (1) is preferably prepared so as to contain ethanol in an amount of about 95 volume % or less, more preferably about 70 volume % or less, and even more preferably about 60 volume % or less. When the ethanol-water mixed solution contains ethanol in an amount of 95 volume % or less, a dihydrate of the benzothiophene compound represented by Formula (I) can be obtained. Although the lower limit of the amount of ethanol in the solution is not particularly limited, it is preferably about 20 volume %, and more preferably about 30 volume %.

The concentration of the benzothiophene compound of Formula (I) in the ethanol-water mixed solution is preferably about 0.1 to 30 wt. % (w/w %), more preferably about 0.5 to 20 wt. %, and even more preferably about 1 to 10 wt. %. When the concentration of the benzothiophene compound of Formula (I) is set to the aforementioned range, the benzothiophene compound of Formula (I) can be fully dissolved in the ethanol-water mixed solution, and a dihydrate with a higher purity can be obtained by performing the subsequent steps (steps (2) and (3)) described below.

The amount of the organic acid in the ethanol-water mixed solution is not particularly limited insofar as the system can be adjusted to an acidic condition. For example, the organic acid is preferably contained in an amount of about 0.1 to 20 wt. %, more preferably about 0.3 to 10 wt. %, and even more preferably about 0.5 to 5 wt. %.

The amount of the organic acid is not particularly limited, insofar as the system can be adjusted to an acidic condition. For example, the organic acid is preferably contained in an amount of about 5 to 100 parts by weight, more preferably about 20 to 80 parts by weight, based on 100 parts by weight of the benzothiophene compound of Formula (I).

The temperature at which the solution is prepared in step (1) is not particularly limited insofar as the following conditions are met: the benzothiophene compound of Formula (I) is dissolved in a liquid containing the aforementioned organic acid and ethanol-water mixed solution; ethanol, water, or the organic acid does not vaporize; and the benzothiophene compound does not decompose. Specifically, the temperature is preferably about 50 to 120° C., and more preferably about 70 to 100° C. A reflux temperature (about 80° C.) may be used.

In step (2), the solution obtained in step (1) is cooled. The cooling temperature is 5° C. or less, preferably about 0° C. or less, and more preferably −2° C. or less. When the pH of the solution is adjusted with an alkali in a subsequent step, heat is generated. Therefore, when the cooling temperature is higher than 5° C., the yield of the dihydrate of the present invention tends to be insufficient. The lower limit of the cooling temperature in step (2) is not particularly limited. However, in view of the fact that the temperature must be raised in the subsequent step and that water may be frozen, the lower limit of the cooling temperature is preferably about −20° C., and more preferably about −10° C.

In step (3), the solution cooled in step (2) is mixed with an alkali to adjust the pH to 7 or more. Examples of the alkali include sodium hydroxide, potassium hydroxide, and the like.

For mixing the solution cooled in step (2) with an alkali, an aqueous alkali solution prepared in advance may be used. The concentration of the aqueous alkali solution is, for example, about 0.1 to 25 wt. %, and more preferably about 0.5 to 10 wt. %.

To avoid a rapid temperature rise of the mixed solution in the system by the addition of an alkali (aqueous solution) as described above, the alkali (aqueous solution) is preferably pre-cooled. The temperature of the alkali (aqueous solution) is preferably about −5 to 15° C., and more preferably about −2 to 5° C.

The amount of alkali is not particularly limited insofar as the solution in the system can be adjusted to a pH of 7 or more. For example, an alkali is preferably added in an amount of about 0.3 to 10 parts by weight, and more preferably about 0.5 to 3 parts by weight, per part by weight of the organic acid incorporated in the solution in step (1).

In step (3), the solution is adjusted with an alkali to a pH of 7 or more, more preferably about 7.5 or more, and still more preferably about 8 or more. When the pH is less than 7, the yield of the dihydrate of the present invention tends to be insufficient. Although the upper limit of the pH is not particularly limited, it is preferably, for example, a pH of about 12, and more preferably a pH of about 10, to facilitate the washing of the precipitated dihydrate of the present invention and the formation of a salt of the benzothiophene compound under strongly alkaline conditions.

By performing steps (1) to (3), the dihydrate of the present invention is precipitated.

The precipitated dihydrate of the present invention is separated into solid and liquid phases by a known method and purified by washing with water.

Preferably, the obtained dihydrate of the benzothiophene compound of Formula (I) or of a salt thereof is heated to about 10° C. or higher, and more preferably about 10 to about 50° C.

Dihydrate of the Benzothiophene Compound of Formula (I) or of a Salt Thereof

The physicochemical properties of the dihydrate of the present invention obtained by the above production process are shown below.

The crystalline form of the dihydrate of the present invention obtained by the above production process may include a hydrate of the benzothiophene compound or of a salt thereof obtained by the above production process according to another embodiment of the present invention.

X-ray Powder Diffraction

The dihydrate of the present invention is identified by an X-ray powder diffraction pattern measured by copper radiation of λ=1.5418 Å through a monochromator. The dihydrate of the present invention has peaks shown in FIG. 2 in the X-ray powder diffraction pattern, and has characteristic peaks at the following diffraction angles (2θ) in the X-ray powder diffraction pattern. These peaks are different from the peaks of the known benzothiophene compound of Formula (I) (in the form of an anhydride).

Diffraction Angles (2θ)
8.1°
8.9°
15.1°
15.6°
24.4°

The dihydrate of the present invention has peaks at the following diffraction angles (2θ) as shown in FIG. 2, in addition to the aforementioned peaks.

Diffraction Angles (2θ)
11.6°, 12.2°, 14.0°, 16.3°, 18.1°, 18.4°, 18.9°, 19.5°, 20.5°, 21.5°, 22.6°, 23.3°, 25.0°, 26.1°, 26.4°, 27.1°, 28.1°, 28.5°, 28.9°, 29.8°, 30.4°, 30.7°, 31.6°, 32.9°, 33.9°, 34.4°, 35.2°, 36.0°, 36.7°, 37.4°, 38.3°.

Although the above diffraction angles (2θ) may contain an error of −0.2 to +0.2° according to the measuring apparatus, measurement conditions, etc., such a level of error is within an acceptable range in the present invention.

Infrared Absorption Measurement

The dihydrate of the present invention is identified by an infrared absorption spectrum measured by the potassium bromide tablet method. In the infrared absorption spectrum, the dihydrate of the present invention has a spectrum shown in FIG. 3, and has peaks at the following wavenumbers ($cm^{-1}$):

Wavenumbers
3509 $cm^{-1}$
2934 $cm^{-1}$
2812 $cm^{-1}$
1651 $cm^{-1}$
1626 $cm^{-1}$
1447 $cm^{-1}$
1223 $cm^{-1}$
839 $cm^{-1}$ The dihydrate of the present invention has peaks at the wavenumbers shown in FIG. 3, in addition to the aforementioned peaks.

Although the wavenumbers ($cm^{-1}$) may contain an error of −0.5 to +0.5% according to the measuring apparatus, measurement conditions, etc., such a level of error is within an acceptable range in the present invention.

The dihydrate of the present invention is identified by a Raman spectrum. The dihydrate of the present invention has the spectrum shown in FIG. 4 and has peaks in the vicinity of the following wavenumbers ($cm^{-1}$):

Wavenumbers
1497 $cm^{-1}$
1376 $cm^{-1}$
1323 $cm^{-1}$
1311 $cm^{-1}$
1287 $cm^{-1}$
1223 $cm^{-1}$
781 $cm^{-1}$ The dihydrate of the present invention has peaks in the vicinity of the following wavenumbers as shown in FIG. 4, in addition to the aforementioned peaks:

Wavenumbers
1656 $cm^{-1}$, 1613 $cm^{-1}$, 1563 $cm^{-1}$, 1512 $cm^{-1}$, 1468 $cm^{-1}$, 1446 $cm^{-1}$, 1241 $cm^{-1}$, 1203 $cm^{-1}$, 1145 $cm^{-1}$, 1096 $cm^{-1}$, 1070 $cm^{-1}$, 971 $cm^{-1}$, 822 $cm^{-1}$ Water Content The dihydrate of the present invention contains water in an amount of 6.5 to 8.8 wt. %, and more specifically 7.3 to 8.1 wt. %. The water content is measured by the Karl Fischer method.

¹H-NMR Measurement

The dihydrate of the present invention is identified by peaks measured by ¹H-NMR spectroscopy. The dihydrate of the present invention has the ¹H-NMR spectrum shown in FIG. 1, and has proton peaks in the ¹H-NMR spectrum measured in Example 1 below.

The hydrate of the benzothiophene compound of Formula (I) according to another embodiment of the present invention is obtained during the process of producing the dihydrate as described above. The physicochemical properties of the hydrate are shown below.

X-ray Powder Diffraction

The hydrate of the benzothiophene compound of Formula (I) according to another embodiment of the present invention has peaks shown in FIG. 10 in an X-ray powder diffraction pattern measured in the same manner as above, and has characteristic peaks at the following diffraction angles (2θ). These peaks are different from the peaks of the known benzothiophene compound of Formula (I) (in the form of an anhydride) in the X-ray powder diffraction pattern.

Diffraction angles (2θ)
7.7°
9.4°
11.8°
18.9°
24.0°

The hydrate of the benzothiophene compound of Formula (I) according to another embodiment of the present invention has peaks at the following diffraction angles (2θ) as shown in FIG. 10, in addition to the aforementioned peaks.

Diffraction Angles (2θ)
5.7°, 8.1°, 8.8°, 10.7°, 12.6°, 13.6°, 13.9°, 15.0°, 15.6°, 16.6°, 17.2°, 17.7°, 19.8°, 20.4°, 21.2°, 21.6°, 22.2°, 23.1°, 25.2°, 25.8°, 26.7°, 27.2°, 27.9°, 28.7°, 29.3°, 30.2°, 31.2°, 33.4°

Benzothiophene Compound Containing the Dihydrate of the Present Invention

The present invention further provides a benzothiophene compound comprising a dihydrate of the benzothiophene compound of Formula (I) or of a salt thereof and an anhydride of the benzothiophene compound of Formula (I) or of a salt thereof. The benzothiophene compound can be used as a therapeutic and/or prophylactic agent for central nervous system diseases.

The benzothiophene compound of Formula (I) or of a salt thereof may consist only of the dihydrate of the present invention or may be in the form of a mixture of the dehydrate of the present invention with a hydrate of the benzothiophene compound of Formula (I) according to another embodiment of the present invention.

The benzothiophene compound preferably contains the dihydrate in an amount of 60 wt. % or more, preferably 80 wt. % or more, and more preferably 90 wt. % or more.

The dihydrate of the present invention may be further pulverized to a desired mean particle diameter. Pulverization methods that can be used include dry-milling processes and wet-milling processes. Examples of mills usable in such milling processes include jet mills, ball mills (e.g., Dyno-Mill), and other low-energy mills (e.g., roller mills), and high-energy mills. Examples of high-energy mills include Netzsch mills, DC mills, planetary mills, and the like. The pulverized dihydrate of the present invention preferably has a mean particle diameter of about 1 to 10 μm, more preferably about 2 to 8 μm, and even more preferably about 2 to 6 μm. The pulverized dihydrate is included within the scope of the dihydrate of the present invention.

The term "mean particle diameter" as used herein refers to the volume mean diameter as measured by a laser-light-scattering (LLS) method. Particle size distribution is measured by an LLS method, and mean particle diameter is calculated from the particle size distribution.

The salt referred to in the dihydrate of the benzothiophene compound of Formula (I) or of a salt thereof is not particularly limited insofar as it is a pharmaceutically acceptable salt. Examples of salts include alkali metal salts (e.g., sodium salts and potassium salts), alkaline earth metal salts (e.g., calcium salts and magnesium salts), and like metal salts; ammonium salts, alkali metal carbonates (e.g., lithium carbonate, potassium carbonate, sodium carbonate, and cesium carbonate), alkali metal hydrogen carbonates (e.g., lithium hydrogen carbonate, sodium hydrogen carbonate, and potassium hydrogen carbonate), alkali metal hydroxides (e.g., lithium hydroxide, sodium hydroxide, potassium hydroxide, and cesium hydroxide), and like salts of inorganic bases; tri(lower)alkylamines (e.g., trimethylamine, triethylamine, and N-ethyldiisopropylamine), pyridine, quinoline, piperidine, imidazole, picoline, dimethylaminopyridine, dimethylaniline, N-(lower)alkyl-morpholines (e.g., N-methylmorpholine), 1,5-diazabicyclo[4.3.0]nonene-5 (DBN), 1,8-diazabicyclo[5.4.0]undecene-7 (DBU), 1,4-diazabicyclo[2.2.2]octane (DABCO), and like salts of organic bases; and hydrochloride, hydrobromate, hydroiodide, sulfate, nitrate, phosphate, and like salts of inorganic acids; formate, acetate, propionate, oxalate, malonate, succinate, fumarate, maleate, lactate, malate, citrate, tartrate, carbonate, picrate, methanesulfonate, ethanesulfonate, p-toluenesulfonate, glutamate, and like salts of organic acids. The term "(lower) alkyl" as used herein refers to an "alkyl having 1 to 6 carbon atoms."

The dihydrate of the benzothiophene compound of Formula (I) or of a salt thereof may be pharmaceutically acceptable co-crystals or co-crystal salts. The term "co-crystal or co-crystal salt" as used herein means a crystalline material comprised of two or more unique solids at room temperature, each containing distinctive physical characteristics (such as structure, melting point, and heat of fusion). Co-crystals and co-crystal salts can be produced according to known co-crystallization methods.

Pharmaceutical Preparation Containing the Dihydrate of the Present Invention

The dihydrate of the present invention is usable as a pharmaceutical preparation for treating central nervous system diseases.

The pharmaceutical preparation is used in the form of an ordinary pharmaceutical preparation, and is prepared using various generally used diluents and excipients, such as fillers, extenders, binders, moisturizing agents, disintegrators, surfactants, lubricants, etc. The form of such a pharmaceutical preparation can be selected according to the purpose of the therapy. Typical examples include tablets, pills, powders, solutions, suspensions, emulsions, granules, capsules, suppositories, injections (solutions, suspensions, etc.) and the like.

To form tablets, any of various carriers conventionally known in this field can be used. Examples thereof include lactose, white sugar, sodium chloride, glucose, urea, starch, calcium carbonate, kaolin, crystalline cellulose, silicic acid, and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminarin powder, sodium hydrogen carbonate, calcium carbonate, fatty acid esters of polyoxyethylene sorbitan, sodium lauryl sulfate, stearic acid monoglycerides, starch, lactose, and other disintegrators; white sugar, stearin, cacao butter, hydrogenated oils, and other disintegration inhibitors; quaternary ammonium bases, sodium lauryl sulfate, and other absorption promoters; glycerol, starch, and other moisturizing agents; starch, lactose, kaolin, bentonite, colloidal silicic acid, and other adsorbents; purified talc, stearates, boric acid powder, polyethylene glycol, and other lubricants; etc. Further, such tablets may be coated with typical coating materials as required, to prepare, for example, sugar-coated tablets, gelatin-coated tablets, enteric-coated tablets, film-coated tablets, double- or multi-layered tablets, etc.

To form pills, any of various carriers conventionally known in this field can be used. Examples thereof include glucose, lactose, starch, cacao butter, hydrogenated vegetable oils, kaolin, talc, and other excipients; powdered acacia, powdered tragacanth, gelatin, ethanol, and other binders; laminarin, agar, and other disintegrators; etc.

To form suppositories, any of various carriers conventionally known in this field can be used. Examples thereof include polyethylene glycol, cacao butter, higher alcohols, esters of higher alcohols, gelatin, semi synthetic glycerides, etc.

Capsules can be prepared by mixing the active ingredient with an above-mentioned carrier and enclosing the result in a hard gelatin capsule, soft capsule, or the like.

To form injectable preparations, a solution, emulsion or suspension is sterilized and preferably made isotonic to blood. Any of the diluents widely used for such forms in this field can be employed to form the injectable preparation. Examples of such diluents include water, ethanol, macrogol, propylene glycol, ethoxylated isostearyl alcohol, polyoxylated isostearyl alcohol, fatty acid esters of polyoxyethylene sorbitan, etc.

In this case, the pharmaceutical preparation may contain sodium chloride, glucose or glycerol in an amount sufficient to prepare an isotonic solution, and may contain conventional solubilizers, buffers, analgesic agents, etc. Further, if necessary, the pharmaceutical preparation may contain coloring agents, preservatives, fragrances, flavors, sweetening agents, etc., and/or other medicines.

The amount of the dihydrate of the present invention contained in the pharmaceutical preparation is not limited, and can be suitably selected from a wide range. The amount is generally about 1 to 70% by weight, and preferably about 1 to 30% by weight of the pharmaceutical preparation.

The route of administration of the pharmaceutical preparation of the present invention is not particularly limited, and the preparation is administered by a route suitable to the form of the preparation, the patient's age, sex and other conditions, and the status of the disease. For example, tablets, pills, solutions, suspensions, emulsions, granules and capsules are administered orally. Injectable preparations are intravenously administered singly or mixed with typical injection transfusions, such as glucose solutions, amino acid solutions or the like, or singly administered intramuscularly, intracutaneously, subcutaneously or intraperitoneally, as required. Suppositories are administered intrarectally.

The dosage of the pharmaceutical preparation of the present invention is suitably selected according to the method of use, the patient's age, sex and other conditions, and the severity of the disease. The amount of active ingredient is usually about 0.1 to 10 mg/kg body weight/day. Further, it is desirable that the pharmaceutical preparation in each unit of the administration form contain the active ingredient in an amount of about 1 to 200 mg.

Specific examples of the central nervous system diseases treated by the pharmaceutical preparation containing the dihydrate of the present invention include schizophrenia, such as treatment-resistant, refractory and chronic schizophrenia, emotional disturbance, psychotic disorder, mood disorder, bipolar disorder (e.g., bipolar I disorder and bipolar II disorder), mania, depression, endogenous depression, major depression, melancholic and treatment-resistant depression, dysthymic disorder, cyclothymic disorder, anxiety disorder (e.g., panic attack, panic disorder, agoraphobia, social phobia, obsessive-compulsive disorder, post traumatic stress disorder, generalized anxiety disorder, and acute stress disorder), somatoform disorder (e.g., hysteria, somatization disorder, conversion disorder, pain disorder, and hypochondria), factitious disorder, dissociative disorder, sexual disorder (e.g., sexual dysfunction, libido disorder, sexual arousal disorder, and erectile dysfunction), eating disorder (e.g., anorexia nervosa and bulimia nervosa), sleep disorder, adjustment disorder, substance-related disorder (e.g., alcohol abuse, alcohol intoxication and drug addiction, amphetamine addiction, and narcotism), anhedonia (e.g., iatrogenic anhedonia, anhedonia of a psychic or mental cause, anhedonia associated with depression, anhedonia associated with schizophrenia), delirium, cognitive impairment, cognitive impairment associated with Alzheimer's disease, Parkinson's disease, and other neurodegenerative diseases, BPSD (Behavioral and Psychological Symptoms of Dementia) caused by cognitive impairment, cognitive impairment in schizophrenia, cognitive impairment caused by treatment-resistant, refractory or chronic schizophrenia, vomiting, motion sickness, obesity, migraine, pain, mental retardation, autistic disorder (autism), Tourette's syndrome, tic disorder, attention deficit hyperactivity disorder, conduct disorder, Down's syndrome, etc.; and various other central nervous system diseases. The pharmaceutical preparation containing the dihydrate of the benzothiophene compound is extremely effective for the amelioration of these central nervous system diseases.

Advantageous Effects of Invention

The present invention provides a novel dihydrate of the benzothiophene compound represented by Formula (I) or of a salt thereof. The present invention also enables the production of a desired dihydrate in an industrially advantageous manner by employing a specific manufacturing method for the benzothiophene compound represented by Formula (I) or a salt thereof.

Furthermore, the present invention is advantageous in that when the dihydrate is used as a drug, its pharmacological effect can be remarkably retained after administration to a patient.

When the dihydrate of the present invention is used as the active ingredient of an intramuscular injectable preparation, stimulation after intramuscular injection is low and thus effective.

BRIEF DESCRIPTION OF DRAWINGS

FIG. 1 shows the $^1$H-NMR spectrum of the dihydrate of the benzothiophene compound represented by Formula (I) prepared in example 1.

FIG. 2 shows the X-ray powder diffraction pattern of the dihydrate of the benzothiophene compound represented by Formula (I) prepared in Example 1.

FIG. 3 shows the infrared absorption spectrum of the dihydrate of the benzothiophene compound represented by Formula (I) prepared in Example 1.

FIG. 4 shows the Raman spectrum of the dihydrate of the benzothiophene compound represented by Formula (I) prepared in example 1.

FIG. 5 shows the $^1$H-NMR spectrum of the benzothiophene compound represented by Formula (I) prepared in Example 2.

FIG. 6 shows the X-ray powder diffraction pattern of the dihydrate of the benzothiophene compound represented by Formula (I) prepared in Example 2.

FIG. 7 shows the infrared absorption spectrum of the dihydrate of the benzothiophene compound represented by Formula (I) prepared in Example 2.

FIG. 8 shows the Raman spectrum of the dihydrate of the benzothiophene compound represented by Formula (I) prepared in Example 2.

FIG. 9 shows the Raman spectrum of the dihydrate of the benzothiophene compound represented by Formula (I) prepared in Example 3.

FIG. 10 shows the X-ray powder diffraction pattern of the dihydrate of the benzothiophene compound represented by Formula (I) prepared in Reference Example 3.

FIG. 11 shows the $^1$H-NMR spectrum of the anhydride of the benzothiophene compound represented by Formula (I) prepared in Comparative Example 1.

FIG. 12 shows the X-ray powder diffraction pattern of the anhydride of the benzothiophene compound prepared in Comparative Example 1.

FIG. 13 shows the infrared absorption spectrum of the anhydride of the benzothiophene compound prepared in Comparative example 1.

FIG. 14 is a graph showing the mean blood concentration-time profile of Compound (I) after being injected into the thigh muscle of a dog.

DESCRIPTION OF EMBODIMENTS

EXAMPLES

The present invention is described in further detail with reference to Examples and Test Examples. However, the scope of the invention is not limited to these Examples.

Reference Example 1

Synthesis of 7-(4-chlorobutoxy)-1H-quinolin-2-one

Methanol (149 L), 7-hydroxy-1H-quinolin-2-one (14.87 kg), and potassium hydroxide (6.21 kg) were mixed and stirred. After dissolution, 1-bromo-4-chlorobutane (47.46 kg) was further added thereto and the resulting mixture was stirred under reflux for seven hours. Thereafter, the mixture was stirred at 10° C. for one hour. The precipitated crystal was centrifuged and washed with methanol (15 L). The wet crystal was collected and placed in a tank. Water (149 L) was added thereto, followed by stirring at room temperature. After centrifugation, the resulting solid was washed with water (30 L). The wet crystal was collected and placed in a tank. After adding methanol (74 L), the mixture was stirred under reflux for one hour, cooled to 10° C., and then stirred. The precipitated crystal was centrifuged and washed with methanol (15 L). The separated crystal was dried at 60° C. to obtain 7-(4-chlorobutoxy)-1H-quinolin-2-one (15.07 kg).

Reference Example 2

Synthesis of 7-[4-(4-benzo[b]thiophen-4-yl-piperazin-1-yl)butoxy]-1H-quinolin-2-one Water (20 L), potassium carbonate (1.84 kg), 1-benzo[b]thiophen-4-yl-piperazine hydrochloride (3.12 kg), and ethanol (8 L) were mixed and stirred at 50° C. 7-(4-Chlorobutoxy)-1H-quinolin-2-one (2.80 kg) obtained in Reference Example 1 was added to the mixture and stirred under reflux for nine hours. After concentrating the solvent (8 L) under ordinary pressure, the mixture was stirred at 90° C. for one hour and then cooled to 9° C. The precipitated crystal was centrifuged and then sequentially washed with water (8 L) and ethanol (6 L). The separated crystal was dried at 60° C. to obtain a crude product. The crude product (4.82 kg) and ethanol (96 L) were mixed in a reaction vessel, and acetic acid (4.8 L) was introduced into the reaction vessel. The mixture was stirred under reflux for one hour to dissolve the crude product. After introducing hydrochloric acid (1.29 kg), the mixture was cooled to 10° C. The mixture was heated again, refluxed for one hour, and cooled to 7° C. The precipitated crystal was centrifuged and washed with ethanol (4.8 L). The separated crystal was dried at 60° C. to obtain 7-[4-(4-benzo[b]thiophen-4-yl-piperazin-1-yl)butoxy]-1H-quinolin-2-one hydrochloride (5.09 kg). The resulting 7-[4-(4-benzo[b]thiophen-4-yl-piperazin-1-yl)butoxy]-1H-quinolin-2-one hydrochloride (5.00 kg), ethanol (45 L), and water (30 L) were mixed in a reaction vessel. The mixture was stirred under reflux to dissolve the 7-[4-(4-benzo[b]thiophen-4-yl-piperazin-1-yl)butoxy]-1H-quinolin-2-one hydrochloride. Activated carbon (500 g) and water (5 L) were added thereto, and an activated carbon treatment was conducted under reflux for 30 minutes. After performing hot filtration, a solution containing sodium hydroxide (511 g) dissolved in water (1.5 L) was flowed into the reaction vessel while stirring the filtrate under reflux. After stirring under reflux for 30 minutes, water (10 L) was introduced thereto and the mixture was cooled to approximately 40° C. The precipitated crystal was centrifuged and washed with water (125 L). The separated crystal was dried at 80° C. to obtain 7-[4-(4-benzo[b]thiophen-4-yl-piperazin-1-yl)butoxy]-1H-quinolin-2-one (3.76 kg).

Example 1

Preparation of 7-[4-(4-benzo[b]thiophen-4-yl-piperazin-1-yl)butoxy]-1H-quinolin-2-one dihydrate The 7-[4-(4-benzo[b]thiophen-4-yl-piperazin-1-yl)butoxy]-1H-quinolin-2-one (3.2 kg) obtained in Reference Example 2, ethanol (64 L), water (74 L), and acetic acid (1.77 kg) were mixed in a reaction vessel to prepare an acidic liquid mixture. The mixture was stirred under reflux to dissolve the 7-[4-(4-benzo[b]thiophen-4-yl-piperazin-1-yl)butoxy]-1H-quinolin-2-one (reflux temperature: 84° C.). After cooling to −5° C., the solution obtained above was introduced, over a period of 30 minutes, into a solution containing 25% sodium hydroxide (5.9 kg) and water (54 L) that was cooled to 0° C., to prepare a liquid mixture with pH10. After being stirred at 5° C. or below for one hour, the mixture was heated to 20 to 30° C. and further stirred for seven hours. The precipitated crystal was filtered and washing with water (320 L) was performed until alkali in the solid component disappeared (i.e., until the pH value of the filtrate became 7). The solid component was then air-dried until its weight became constant to obtain a white solid 7-[4-(4- benzo[b]thiophen-4-yl-piperazin-1-yl)butoxy]-1H-quinolin-2-one dihydrate (unground, 3.21 kg).

FIG. 1 shows the $^1$H-NMR spectrum (DMSO-d$_6$, TMS) of the dihydrate prepared by the aforesaid method. As shown in FIG. 1, in the $^1$H-NMR spectrum (DMSO-d$_6$, TMS), peaks were observed at 1.64 ppm (tt, J=7.4 Hz, J=7.4 Hz, 2H), 1.80 ppm (tt, J=7.0 Hz, J=7.0 Hz, 2H), 2.44 ppm (t, J=7.5 Hz, 2H), 2.62 ppm (br, 4H), 3.06 ppm (br, 4H), 3.32 ppm (s, 4H+H$_2$O), 4.06 ppm (t, J=6.5 Hz, 2H), 6.29 ppm (d, J=9.5 Hz, 1H), 6.80 ppm (d, J=2.5 Hz, 1H), 6.80 ppm (dd, J=2.5 Hz, J=9.0 Hz, 1H), 6.88 ppm (d, J=7.5 Hz, 1H), 7.27 ppm (dd, J=7.8 Hz, J=7.8 Hz, 1H), 7.40 ppm (dd, J=0.5 Hz, J=5.5 Hz, 1H), 7.55 ppm (d, J=9.0 Hz, 1H), 7.61 ppm (d, J=8.0 Hz, 1H), 7.69 ppm (d, J=5.5 Hz, 1H), 7.80 ppm (d, J=9.5 Hz, 1H), and 11.57 ppm (s, 1H).

The X-ray powder diffraction spectrum of the dihydrate prepared by the aforesaid method was measured using an X-ray diffractometer (D8 ADVANCE, available from Bruker AXS). FIG. 2 shows the X-ray powder diffraction spectrum. As shown in FIG. 2, in the X-ray powder diffraction spectrum, diffraction peaks were observed at 2θ=8.1°, 8.9°, 15.1°, 15.6°, and 24.4°. Other than those mentioned above, the diffraction peaks were also observed at 2θ=11.6°, 12.2°, 14.0°, 16.3°, 18.1°, 18.4°, 18.9°, 19.5°, 20.5°, 21.5°, 22.6°, 23.3°, 25.0°, 26.1°, 26.4°, 27.1°, 28.1°, 28.5°, 28.9°, 29.8°, 30.4°, 30.7°, 31.6°, 32.9°, 33.9°, 34.4°, 35.2°, 36.0°, 36.7°, 37.4°, and 38.3°.

The IR (KBr) spectrum of the dihydrate prepared by the aforesaid method was measured. FIG. 3 shows the IR (KBr) spectrum. As shown in FIG. 3, in the IR (KBr) spectrum, absorption bands were observed in the vicinity of wavenumbers 3509 cm$^{-1}$, 2934 cm$^{-1}$, 2812 cm$^{-1}$, 1651 cm$^{-1}$, 1626 cm$^{-1}$, 1447 cm$^{-1}$, 1223 cm$^{-1}$ and 839 cm$^{-1}$.

The Raman spectrum of the dihydrate prepared by the aforesaid method was measured. FIG. 4 shows the Raman spectrum. As shown in FIG. 4, in the Raman spectrum, absorption bands were observed in the vicinity of wavenumbers 1497 cm$^{-1}$, 1376 cm$^{-1}$, 1323 cm$^{-1}$, 1311 cm$^{-1}$, 1287 cm$^{-1}$, 1223 cm$^{-1}$, and 781 cm$^{-1}$.

Other than those mentioned above, absorption was also observed in the vicinity of wavenumbers 1656 cm$^{-1}$, 1613 cm$^{-1}$, 1563 cm$^{-1}$, 1512 cm$^{-1}$, 1468 cm$^{-1}$, 1446 cm$^{-1}$, 1241 cm$^{-1}$, 1203 cm$^{-1}$, 1145 cm$^{-1}$, 1096 cm$^{-1}$, 1070 cm$^{-1}$, 971 cm$^{-1}$, and 822 cm$^{-1}$.

The water content of the dihydrate prepared by the aforesaid method was measured using a moisture meter (CA-100, available from Mitsubishi Chemical Analytech Co., Ltd.) by the Karl Fischer method. As a result, the dihydrate had a water content of 7.79% by weight.

Example 2

Preparation of Finely Ground Dihydrate

Dihydrate crystal (2.73 kg) obtained in Example 1 was ground using a jet mill. Here, the air pressure was set at 5 kgf/cm$^2$, and the rotational speed of the feeder was set at 20 rpm. As a result, finely ground 7-[4-(4-benzo[b]thiophen-4-yl-piperazin-1-yl)butoxy]-1H-quinolin-2-one dihydrate (2.61 kg, 95.6%) was obtained.

The dihydrate (finely ground product) thus obtained had a mean particle diameter of 5.5 μm. The mean particle diameter was measured using a Microtrack HRA, manufactured by Nikkiso Co., Ltd.

FIG. 5 shows the $^1$H-NMR spectrum (DMSO-d$_6$, TMS) of the dihydrate prepared by the above method. As shown in FIG. 5, in the $^1$H-NMR spectrum (DMSO-d$_6$, TMS), peaks were observed at 1.64 ppm (tt, J=7.3 Hz, J=7.3 Hz, 2H), 1.80 ppm (tt, J=6.9 Hz, J=6.9 Hz, 2H), 2.44 ppm (t, J=7.3 Hz, 2H), 2.62 ppm (br, 4H), 3.06 ppm (br, 4H), 3.32 ppm (s, 4H+H$_2$O), 4.06 ppm (t, J=6.5 Hz, 2H), 6.29 ppm (d, J=9.5 Hz, 1H), 6.80 ppm (d, J=2.5 Hz, 1H), 6.80 ppm (dd, J=2.3 Hz, J=9.3 Hz, 1H), 6.88 ppm (d, J=7.5 Hz, 1H), 7.27 ppm (dd, J=8.0 Hz, J=8.0 Hz, 1H), 7.40 ppm (d, J=5.5 Hz, 1H), 7.55 ppm (d, J=9.5 Hz, 1H), 7.61 ppm (d, J=8.0 Hz, 1H), 7.69 ppm (d, J=5.5 Hz, 1H), 7.80 ppm (d, J=9.5 Hz, 1H), and 11.57 ppm (s, 1H).

The X-ray powder diffraction spectrum of the dihydrate prepared by the aforesaid method was measured in the same manner as in Example 1. FIG. 6 shows the X-ray powder diffraction spectrum. As shown in FIG. 6, in the X-ray powder diffraction spectrum, diffraction peaks were observed at 2θ=8.2°, 8.9°, 15.2°, 15.7° and 24.4°.

Other than those mentioned above, the diffraction peaks were also observed at 2θ=6.8°, 12.2°, 14.0°, 14.5°, 17.4°, 18.1°, 18.5°, 19.0°, 19.2°, 19.6°, 20.3°, 20.6°, 21.5°, 22.7°, 23.4°, 25.0°, 26.1°, 27.1°, 28.6°, 29.0°, 30.4°, 34.0°, 34.5°, 35.3°, and 36.7°.

The IR (KBr) spectrum of the dihydrate prepared by the aforesaid method was measured in the same manner as in Example 1. FIG. 7 shows the IR (KBr) spectrum. As shown in FIG. 7, in the IR (KBr) spectrum, absorption bands were observed in the vicinity of wavenumbers 3507 cm$^{-1}$, 2936 cm$^{-1}$, 2812 cm$^{-1}$, 1651 cm$^{-1}$, 1626 cm$^{-1}$, 1447 cm$^{-1}$, 1223 cm$^{-1}$ and 839 cm$^{-1}$.

The Raman spectrum of the dihydrate prepared by the aforesaid method was measured. FIG. 8 shows the Raman spectrum. As shown in FIG. 8, in the Raman spectrum, absorption bands were observed in the vicinity of wavenumbers 1496 cm$^{-1}$, 1376 cm$^{-1}$, 1323 cm$^{-1}$, 1311 cm$^{-1}$, 1286 cm$^{-1}$, 1223 cm$^{-1}$, and 781 cm$^{-1}$.

Other than those mentioned above, absorption was also observed in the vicinity of wavenumbers 1656 cm$^{-1}$, 1614 cm$^{-1}$, 1563 cm$^{-1}$, 1512 cm$^{-1}$, 1467 cm$^{-1}$, 1446 cm$^{-1}$, 1241 cm$^{-1}$, 1203 cm$^{-1}$, 1145 cm$^{-1}$, 1095 cm$^{-1}$, 1069 cm$^{-1}$, 971 cm$^{-1}$, and 822 cm$^{-1}$.

The water content of the dihydrate prepared by the aforesaid method was measured using a moisture meter (CA-100, available from Mitsubishi Chemical Analytech Co., Ltd.) by the Karl Fischer method. As a result, the dihydrate had a water content of 6.74% by weight.

Example 3

Preparation of 7-[4-(4-benzo[b]thiophen-4-yl-piperazin-1-yl)butoxy]-1H-quinolin-2-one dihydrate 7-[4-(4-Benzo[b]thiophen-4-yl-piperazin-1-yl)butoxy]-1H-quinolin-2-one (5.0 kg), ethanol (100 L), water (115 L), and DL-lactic acid (2.29 kg) were mixed to prepare an acidic liquid mixture. The liquid mixture was stirred under reflux to dissolve the 7-[4-(4-benzo[b]thiophen-4-yl-piperazin-1-yl)butoxy]-1H-quinolin-2-one (reflux temperature: 82° C.). After cooling to −5° C., the solution obtained above was introduced, over a period of about 15 minutes, into a solution containing sodium hydroxide (1.48 kg) and water (135 L) that was cooled to 1° C., to prepare a liquid mixture with pH11. After being stirred at approximately 2 to 5° C. for three hours, the mixture was heated to 45° C. and further stirred at 45 to 50° C. for two hours. The precipitated crystal was filtered and washing with water (200 L) was performed until alkali in the solid component disappeared (i.e., until the pH value of the filtrate became 7). The solid component was further washed with a liquid mixture of ethanol (15 L) and water (20 L). The solid component was then dried at room temperature until its weight became constant to obtain a white solid 7-[4-(4-benzo[b]thiophen-4-yl-piperazin-1-yl)butoxy]-1H-quinolin-2-one dihydrate (unground, 5.11 kg).

The dihydrate thus obtained was the same as that obtained in Example 1.

The Raman spectrum of the dihydrate prepared by the aforesaid method was measured. FIG. 9 shows the Raman spectrum.

As shown in FIG. 9, in the Raman spectrum, absorption bands were observed in the vicinity of wavenumbers 1497 $cm^{-1}$, 1376 $cm^{-1}$, 1323 $cm^{-1}$, 1311 $cm^{-1}$, 1287 $cm^{-1}$, 1223 $cm^{-1}$, and 782 $cm^{-1}$.

Other than those mentioned above, absorption was also observed in the vicinity of wavenumbers 1656 $cm^{-1}$, 1614 $cm^{-1}$, 1563 $cm^{-1}$, 1512 $cm^{-1}$, 1468 $cm^{-1}$, 1446 $cm^{-1}$, 1241 $cm^{-1}$, 1203 $cm^{-1}$, 1145 $cm^{-1}$, 1126 $cm^{-1}$, 1096 $cm^{-1}$, 1070 $cm^{-1}$, 972 $cm^{-1}$, and 822 $cm^{-1}$.

Reference Example 3

7-[4-(4-Benzo[b]thiophen-4-yl-piperazin-1-yl)butoxyl]-1H-quinolin-2-one anhydride (7 g), ethanol (140 mL), water (161 mL), and lactic acid (2.7 mL) were mixed in a reaction vessel. The mixture was heated to reflux while being stirred to dissolve the 7-[4-(4-benzo[b]thiophen-4-yl-piperazin-1-yl)butoxy]-1H-quinolin-2-one anhydride. After being cooled to approximately −10° C., the solution obtained above was introduced, while being stirred, into a solution containing sodium hydroxide (2.1 g) and water (189 mL) that was cooled to approximately 0° C. After being stirred at a temperature of approximately 0° C. for 3 hours, solid-liquid separation was performed.

The X-ray powder diffraction spectrum of the hydrate prepared by the aforesaid method was measured in the same manner as in Example 1. FIG. 10 shows the X-ray powder diffraction spectrum. In the X-ray powder diffraction spectrum, diffraction peaks were observed at 2θ=7.7°, 9.4°, 11.8°, 18.9°, and 24.0°. Other than those mentioned above, diffraction peaks were also observed at 2θ=5.7°, 8.1°, 8.8°, 10.7°, 12.6°, 13.6°, 13.9°, 15.0°, 15.6°, 16.6°, 17.2°, 17.7°, 19.8°, 20.4°, 21.2°, 21.6°, 22.2°, 23.1°, 25.2°, 25.8°, 26.7°, 27.2°, 27.9°, 28.7°, 29.3°, 30.2°, 31.2°, and 33.4°.

Comparative Example 1

Preparation of 7-[4-(4-benzo[b]thiophen-4-yl-piperazin-1-yl)butoxy]-1H-quinolin-2-one anhydride The 7-[4-(4-benzo[b]thiophen-4-yl-piperazin-1-yl)butoxy]-1H-quinolin-2-one (700 g) prepared in Reference Example 2, ethanol (14 L), and acetic acid (1.4 L) were mixed in a reaction vessel. The mixture was heated to the reflux temperature (76° C.) to dissolve 7-[4-(4-benzo[b]thiophen-4-yl-piperazin-1-yl)butoxy]-1H-quinolin-2-one. Concentrated hydrochloric acid (158 mL) was further added thereto and then cooled to 10° C. while being stirred. Thereafter, the mixture was heated again, stirred under reflux for one hour, and then cooled to 8° C. The precipitated solid was filtered by suction and washed with ethanol (0.7 L). The solid component was then dried at 60° C. until its weight became constant to obtain a white solid 7-[4-(4-benzo[b]thiophen-4-yl-piperazin-1-yl)butoxy]-1H-quinolin-2-one hydrochloride (814 g). 7-[4-(4-Benzo[b]thiophen-4-yl-piperazin-1-yl)butoxy]-1H-quinolin-2-one hydrochloride (800 g), ethanol (7.2 L), and water (4.8 L) were mixed in a reaction vessel, and the mixture was heated to the reflux temperature (80° C.) while being stirred. After performing hot filtration, the mixture was heated again to 78° C., and the crystal precipitated in the filtrate was dissolved. A solution containing sodium hydroxide (81.6 g) dissolved in water (240 mL) was flowed into the above-obtained solution and the mixture was stirred under reflux for 30 minutes. Water (2.4 L) was added to the mixture, followed by cooling to 40° C. while being stirred. The precipitated solid was filtered and washed with water (16 L). The solid was dried at 80° C. to obtain a white solid 7-[4-(4-benzo[b]thiophen-4-yl-piperazin-1-yl)butoxy]-1H-quinolin-2-one anhydride (637 g).

The $^1$H-NMR spectrum of the anhydride obtained above was measured in the same manner as in Example 1. FIG. 11 shows the $^1$H-NMR spectrum (DMSO-$d_6$, TMS). As shown in FIG. 11, in the $^1$H-NMR spectrum (DMSO-$d_6$, TMS), peaks were observed at 1.63 ppm (tt, J=7.3 Hz, J=7.1 Hz, 2H), 1.80 ppm (tt, J=7.3 Hz, J=6.3 Hz, 2H), 2.44 ppm (t, J=7.1 Hz, 2H), 2.61 ppm (m, 4H), 3.05 ppm (m, 4H), 4.05 ppm (t, J=6.3 Hz, 2H), 6.29 ppm (d, J=9.5 Hz, 1H), 6.80 ppm (d, J=2.5 Hz, 1H), 6.80 (dd, J=9.4 Hz, J=2.5 Hz, 1H), 6.88 ppm (dd, J=7.8 Hz, 0.8 Hz, 1H), 7.27 ppm (dd, J=7.8 Hz, J=7.8 Hz, 1H), 7.39 ppm (dd, J=5.6 Hz, 0.8 Hz, 1H), 7.55 ppm (d, J=9.4 Hz, 1H), 7.61 ppm (d, J=7.8 Hz, 1H), 7.69 ppm (d, J=5.6 Hz, 1H), 7.80 ppm (d, J=9.5 Hz, 1H), and 11.60 (s, 1H).

The X-ray powder diffraction spectrum of the anhydride obtained above was measured in the same manner as in Example 1. FIG. 12 shows the X-ray powder diffraction spectrum. As shown in FIG. 12, in the X-ray powder diffraction spectrum, diffraction peaks were observed at 2θ=14.4°, 19.1°, 20.2°, 21.3°, and 23.2°.

The IR (KBr) spectrum of the anhydride obtained above was measured in the same manner as in Example 2. FIG. 13 shows the IR (KBr) spectrum. As shown in FIG. 13, the 7-[4-(4-benzo[b]thiophen-4-yl-piperazin-1-yl)butoxy]-1H-quinolin-2-one had absorption bands in the IR (KBr) spectrum in the vicinity of wavenumbers 2941 $cm^{-1}$, 2818 $cm^{-1}$, 1655 $cm^{-1}$, 1624 $cm^{-1}$, 1449 $cm^{-1}$, 1221 $cm^{-1}$, and 833 $cm^{-1}$.

The water content of the anhydride prepared by the aforesaid method was measured in the same manner as in Example 2. The result revealed that the anhydride that was obtained had a water content of 0.04% by weight.

Test Example 1

Measurement of Drug Residue in Muscle

The dihydrate of the present invention (150 mg) was dispersed to the suspension medium (1 mL) described below, and pulverized using 5 mm zirconia beads (1.2 g, pulverization time: 30 min) while being stirred with a stirrer. The suspension medium used for pulverization was a solution containing 0.832% (w/v) sodium carboxymethylcellulose (CMC-Na), 4.16% (w/v) mannitol, and 0.074% (w/v) sodium dihydrogenphosphatemonohydrate. The pH thereof was adjusted to 7.0 by adding an appropriate amount of sodium hydroxide. The concentration of each preparation was adjusted to 100 mg/mL using this medium.

The dihydrate (finely ground product) thus obtained had a mean particle diameter of 3.5 μm. An anhydride was subjected to pulverization in the same manner to obtain an anhydride (finely ground product) having a mean particle diameter of 3.5 μm. The mean particle diameter was measured using a laser diffraction particle size analyzer (SALD-3000) or SALD-3100, manufactured by Shimadzu Corporation).

Injectable preparations each containing the dihydrate of the present invention (finely ground product, mean particle diameter: 3.5 μm) or an anhydride (finely ground product, mean particle diameter: 3.5 μm) were obtained by the procedure described above. Table 1 shows the formulations thereof.

Each injectable preparation thus obtained was intramuscularly injected into a rat in a dosage of 25 mg/kg. Each injectable preparation was injected into three rats. 56 days after the injection, the rats were dissected, and the number of rats exhibiting drug residue in muscle was counted. Table 2 shows the results.

TABLE 1

| Formulations | |
| --- | --- |
| Active ingredient | 100 mg |
| Sodium carboxymethylcellulose | 8.32 mg |
| Mannitol | 41.6 mg |
| Sodium dihydrogenphosphate monohydrate | 0.74 mg |
| Sodium hydroxide | Q.S. (adjusted to pH 7) |
| Distilled water | Q.S. |
| Total | 1 mL |

TABLE 2

| Active ingredient | The number having residue in muscle (Number having residue/Total) |
| --- | --- |
| Dihydrate | 3/3 |
| Anhydride | 0/3 |

Test Example 2

Pharmacokinetics Test Using a Dog

Injectable preparations containing the dihydrate of the present invention as an active ingredient were formulated as shown in Table 3. Each of the injectable preparations was injected into the thigh muscle of a dog in such a dosage that 10 mg/kg of active ingredient calculated as the anhydride of the present invention was contained. FIG. 14 is a graph showing the mean blood concentration-time profile after the injection. As is clear from FIG. 14, the sustained release property can be stably maintained for more than 30 days from the injection. Stimulation at the injection site was observed 7 days after the injection and the results showed that the stimulation was low.

TABLE 3

| Test Example 2 | |
| --- | --- |
| Component | Amount (mg) |
| Dihydrate of the present invention | 108 |
| Sorbitol | 50 |
| Sodium carboxymethylcellulose | 10 |
| Sodium dihydrogenphosphate dihydrate | 0.78 |
| Benzyl benzoate | 1 |
| Polysorbate 80 | 2 |
| Sodium hydroxide | Q.S. (pH 7.0) |
| Injection water | Q.S. |
| Total | 1 mL |

The invention claimed is:

1. A process for producing a dihydrate of 7-[4-(4-benzo[b]thiophen-4-yl-piperazin-1-yl)butoxy]-1H-quinolin-2-one or of a salt thereof, the process comprising:

(1) mixing at least one organic acid selected from the group consisting of acetic acid and lactic acid, an ethanol-water mixed solution, and 7-[4-(4-benzo[b]thiophen-4-yl-piperazin-1-yl)butoxy]-1H-quinolin-2-one to prepare an acid solution;

(2) cooling the solution obtained in step (1) to 5° C. or less; and (3) mixing the solution cooled in step (2) with an alkali to adjust the pH of the solution to 7 or more.

2. The process according to claim 1, wherein an alkali is added in an amount of about 0.3 to 10 parts by weight per part by weight of the organic acid incorporated in the solution in step (1).

3. The process according to claim 1, further comprising (4) washing the precipitated dihydrate with water.

* * * * *